United States Patent [19]

Goldberg

[11] Patent Number: 4,512,660
[45] Date of Patent: Apr. 23, 1985

[54] PICOSECOND BROADBAND CARS PROBE USING THE PICOSECOND CONTINUUM

[75] Inventor: Lawrence S. Goldberg, Alexandria, Va.

[73] Assignee: The United States of America as represented by the Secretary of the Navy, Washington, D.C.

[21] Appl. No.: 484,810

[22] Filed: Apr. 14, 1983

[51] Int. Cl.³ .................... G01J 3/44; G01N 21/65
[52] U.S. Cl. .................................................. 356/301
[58] Field of Search ........................................ 356/301

[56] References Cited

U.S. PATENT DOCUMENTS

| | | | |
|---|---|---|---|
| 3,782,828 | 1/1974 | Alfano et al. | 356/301 |
| 3,802,777 | 3/1974 | Regnier et al. | 356/301 |
| 4,008,961 | 2/1977 | Barrett et al. | 356/301 |
| 4,077,719 | 3/1978 | Barrett et al. | 356/301 |
| 4,084,100 | 4/1978 | Begley et al. | 250/574 |
| 4,127,329 | 11/1978 | Chang et al. | 356/301 |
| 4,195,930 | 4/1980 | Delhaye et al. | 356/301 |
| 4,239,390 | 12/1980 | Scherer | 356/301 |
| 4,269,509 | 5/1981 | Berry et al. | 356/301 |
| 4,270,864 | 6/1981 | Barrett et al. | 356/301 |
| 4,405,237 | 9/1983 | Manuccia et al. | 356/301 |

OTHER PUBLICATIONS

D. K. Sharma et al., "Generation of an Intense Picosecond Continuum in D₂O by a Single Picosecond 1.06 Pulse", Chemical Physics Lett., vol. 41, No. 3, Aug. 1, 1976, p. 460.
W. M. Tolles et al., "A Review of the Theory and Application of Coherent Anti-Stokes Raman Spectroscopy (CARS)", Applied Spectroscopy, vol. 31, No. 4, 1977, p. 253.
W. M. Hetherington III, et al., "Picosecond Cars as a Probe of the Multiphoton Photofragmentation of Benzene", Chemical Physcis Lett., vol. 77, No. 2, Jan. 15, 1981, p. 275.
W. B. Roh, "Single-Pulse Coherent Anti-Stokes Raman Scattering", Applied Physcis Lett., vol. 29, No. 3, Aug. 1976, p. 174.
P. R. Regnier et al., "Gas Concentration Measurement by Coherent Raman Anti-Stokes Scattering", Paper given at AIAA 6th Fluid & Plasma Dynamics Conference, Palm Springs, Calif., Jul. 16–18, 1973, (Paper No. 73–702).
G. K. Klauminzer, "Coherent Anti-Stokes Raman Spectroscopy (CARS)", Conference: Laser 77 Opto-Electronics, Munich, Germany; Jun. 20–24, 1977.
F. M. Kamga et al., "Pulse-Sequenced Coherent Anti-Stokes Raman Scattering Spectroscopy: A Method for Suppression of the Nonresonant Background", Optics Lett., vol. 5, No. 3, Mar. 1980, p. 126.

*Primary Examiner*—F. L. Evans
*Attorney, Agent, or Firm*—Robert F. Beers; William T. Ellis; John L. Forrest

[57] ABSTRACT

A coherent anti-Stokes Raman spectroscopy (CARS) method and apparatus for producing a broadband CARS vibrational spectrum of a sample in a single picosecond laser pulse. A laser pulse having a picosecond duration and a frequency of $\omega$ is directed into a liquid cell containing D₂O which generates a picosecond continuum pulse having a broad range of frequencies $\omega_{WL}$ and a picosecond duration. A second harmonic of the laser pulse is produced to form a probe pulse having a frequency of $\omega_1$ and a picosecond duration. The probe pulse and the continuum pulse are spatially and temporally combined and the combined pulses are directed into a sample to excite the Raman active vibrational resonances in the sample. In response the sample emits a beam of radiation which contains an anti-Stokes spectrum of energy characteristic of the sample. The anti-Stokes spectrum is separated from the beam of radiation for detection and analysis.

28 Claims, 4 Drawing Figures

PICOSECOND BROADBAND CARS PROBE USING THE PICOSECOND CONTINUUM

BACKGROUND OF THE INVENTION

The present Invention relates, in general, to a novel coherent anti-Stokes Raman spectroscopy (CARS) method and to a novel apparatus for carrying out this method.

Methods of obtaining broadband, or multiplexed, coherent anti-Stokes Raman spectroscopy (herein often referred to as CARS) spectra in a single laser shot have previously been accomplished on the nanosecond time scale. These methods have used untuned broadband dye laser sources to provide a continuous band of visible Stokes frequencies for the CARS four-wave mixing process. However, the untuned dye lasers have outputs extending over only several hundred wave numbers for a particular dye used and do not lend themselves readily to subnanosecond operation.

The ability to perform optical spectroscopy in the picosecond range is highly desirable in order to observe dynamical phenomena occuring on a time scale of picoseconds. Picosecond applications of CARS have to date only been carried out with the use of narrow-band tunable Stokes frequencies, thus necessitating many laser shots to build up a point-by-point spectrum. Such approaches are not practical for acquiring extensive vibrational spectra of transient, non-repetitive events.

Picosecond white-light continuum pulses have previously been used in optical spectroscopy including a method called inverse Raman scattering. An example of this process is described in U.S. Pat. No. 3,782,828 to ALFANO et al. Inverse Raman scattering, while also providing broadband vibrational spectra, is a Raman absorption process which is distinctly different in approach and applicability from the CARS emission process.

SUMMARY OF THE INVENTION

Accordingly, one object of the present Invention is to provide a novel method and apparatus for obtaining a CARS vibrational spectrum having time resolution on the order of picoseconds.

Another object is to provide a novel method and apparatus for obtaining an extensive broadband CARS vibrational spectrum using a single picosecond laser pulse.

These and other objects and advantages are provided by a novel CARS method and apparatus according to the present Invention which produces a broadband CARS vibrational spectrum of a sample. A probe pulse of coherent monochromatic radiation is generated having a frequency $\omega_1$ and a duration on the order of picoseconds. A continuum pulse of broadband radiation is also generated. The continuum pulse has a range of frequencies $\omega_{WL}$ and a duration on the order of picoseconds. The range of frequencies $\omega_{WL}$ of the continuum pulse and the frequency $\omega_1$ of the probe pulse are related such that the difference $\omega_1 - \omega_{WL}$ corresponds to a range of Raman active vibrational resonances in the sample. The probe pulse and the continuum pulse are spatially and temporally combined and the combined pulses are directed into the sample to excite the sample's Raman-active vibrational resonances. In response to the combined pulses, the sample emits a beam of radiation. The beam of radiation includes an anti-Stokes spectrum of energy characteristic of the sample which is detected.

BRIEF DESCRIPTION OF THE DRAWINGS

A more complete appreciation of the Invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

The present Invention is based upon the application of a picosecond white-light continuum pulse to the CARS process. In the CARS process, two synchronized laser pulses, one of fixed frequency $\omega_1$ and the other of tunable frequency $\omega_2$, mix optically in a molecular sample under study via the third-order non-linear susceptibility $\chi(3)$. When the frequency difference $(\omega_1 - \omega_2)$ is tuned to resonance with a Raman-active vibrational transition, the susceptibility becomes large and an intense blue-shifted anti-Stokes beam at the frequency $\omega_3 = 2\omega_1 - \omega_2$ is generated.

The present Invention replaces the tunable pulse $\omega_2$ with a picosecond white-light continuum pulse $\omega_{WL}$ thereby utilizing the continuum pulse to provide a spectrally broadband picosecond pulse at the Stokes frequencies $\omega_2$. Thus, a complete spectrum may be developed using a single laser shot and the need to build up a point-by-point spectrum by means of multiple shots is eliminated.

Figure 1:
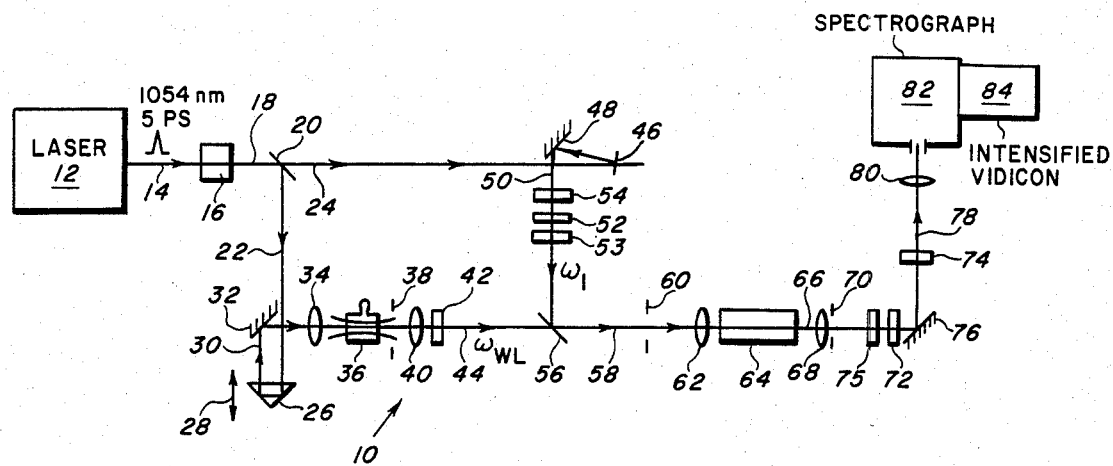
FIG. 1 schematically illustrates a preferred embodiment of the present Invention.

Referring now to the drawings, wherein like reference numerals designate identical or corresponding parts throughout the several views, and more particularly to FIG. 1 thereof, a CARS apparatus 10 for carrying out the method of the present Invention is illustrated. In the CARS apparatus 10, a mode-locked Nd:phosphate glass laser system 12 produces an intense (25 mJ) 1054 nm pulse 14 having a nominal duration of 5 picoseconds. Other mode-locked laser systems, such as Nd:YAG and dye lasers may also be used. Such mode-locked laser systems are well-known in the art and thus will not be described in detail herein.

The 1054 nm pulse 14 is passed through a second-harmonic generator 16 which produces a nominal 5 picosecond output pulse 18 containing the fundamental frequency at 1054 nm and the second harmonic at 527 nm. The second-harmonic generator 16 is formed from a well-known angle-tuned potassium dihydrogen phosphate (KDP) crystal having a thickness of 2 cm.

The pulse 18 is directed onto a spectral beam splitter 20 which separates the frequency components of the pulse. The spectral beam splitter 20 directs the 1054 nm portion of the pulse 18 along an optical path 22 while the 527 nm portion of the pulse 18 is directed along an optical path 24. The spectral beam splitter 20 is formed from a dielectric coated mirror, as is well-known in the art.

The 1054 nm pulse traveling along the optical path 22 passes through a right angle prism 26 which is mounted in a well-known manner to be movable in the directions indicated by arrows 28. The prism 26 redirects the pulse traveling along the optical path 22 to travel along the optical path 30. Additionally, moving the prism 26 allows the length of the optical path traveled by the pulse to be adjusted, thereby introducing a controllable amount of delay into the system, as will be further discussed below.

The 1054 nm pulse traveling along the optical path 30 is redirected by a mirror 32 and focused by a lens 34 into a liquid cell 36 filled with $D_2O$ liquid. Through various non-linear processes in the $D_2O$ liquid, the spectral content of the intense 1054 nm pulse is broadened throughout the near infrared and visible regions. The output of the liquid cell 36 is thus a nominally 5 picosecond duration continuum pulse of essentially white light and includes remanants of the fundamental 1054 nm pulse. In a practical embodiment, the lens 34 had a focal length of 15 cm and the liquid cell 36 had a length of 5 cm. A pulse energy of 10 mJ has proven adequate to produce a satisfactory continuum pulse. Non-linear continuum generators are known in the art. Such generators are described by D. K. SHARMA et al. in Chemical Physics Letters, Vol. 41, No. 3, pp. 460–465, Aug. 1 1976 and in U.S. Pat. No. 3,782,828 to Alfano et al. Other liquid or solid media may be used in the cell 36 for continuum generation. For example, a 50 percent mixture of $D_3PO_4$ and $D_2O$ has proven to produce a spectrally more uniform continuum than that produced by 100 percent $D_2O$ although the output has a lower intensity.

The output of the liquid cell 36 passes through an aperture 38 which eliminates all but an intense central core of the output. The output is then collimated by a lens 40 and passed through a band-pass filter 42 which removes the 1054 nm fundamental wavelength and removes continuum wavelengths below about 550 nm. The output 44 of the filter 42 is an intense 5 picosecond continuum pulse $\omega_{WL}$ at the desired Stokes frequencies $\omega_2$. The filter 42 is a composite filter formed by a standard Schott ™ KG-3 filter and a Schott ™ OG-550 filter.

The 527 nm pulse traveling along the optical path 24 from the beam splitter 20 is reflected by a spectral beam splitter 46 and a mirror 48 to travel along an optical path 50. The beam splitter 46 and the mirror 48 are included to equalize the path length traveled by the 527 nm pulse to that traveled by the continuum pulse $\omega_{WL}$.

The 527 nm pulse traveling along the optical path 50 serves as the pump frequency $\omega_1$ or probe pulse for the four-wave CARS interaction. The pulse $\omega_1$ has a near transform-limited spectral width of approximatey 4 cm$^{-1}$ and thus defines the spectral resolution of the process.

A half-wave plate polarization rotator 54 may be included along the optical path 50, if desired, to alter the state of polarization of the probe pulse $\omega_1$. Certain CARS measurements require the use of probe pulses with appropriately adjusted polarization, as is well known in the art.

The probe pulse $\omega_1$ generated as described above is harmonically related to the 1054 nm fundamental pulse 14 due to the operation of the second-harmonic generator 16. Under some circumstances it may be desirable to use probe pulses having different frequencies. This may be accomplished by including an appropriate frequency shifter 52 along the optical path 50 to alter the frequency of the probe pulse. The frequency shifter 52 may operate by stimulated Raman scattering or by other well-known means. The ouput of the frequency shifter 52 should be passed through an appropriate bandpass filter 53, centered at the desired probe frequency $\omega_1$, to remove any undesired frequency components.

The probe pulse $\omega_1$ and the continuum pulse $\omega_{WL}$ are spatially combined by means of a beam splitter 56, the output of which is directed along an optical axis 58. The pulses $\omega_1$ and $\omega_{WL}$ are temporally combined at the beam splitter 56 by appropriate adjustment of the movable prism 26.

The combined pulses $\omega_1$ and $\omega_{WL}$ are passed through an aperture 60 and are collinearly focused by means of a lens 64 into a sample cell 64 containing a sample of the material to be analysed. The aperture is included to aid in alignment and positioning of the two pulses $\omega_1$ and $\omega_{WL}$. The sample to be analysed may be gaseous, condensed liquid, or solid media. Condensed-phase media will require attention to non-collinear phase matching of the wavevectors for the four-wave interaction, as is well known in the art.

The output 66 of the sample cell 64 is an anti-Stokes beam generated from the sample media under analysis in a single laser shot which contains the spectrum of frequencies $\omega_3$ corresponding to the molecular sample system's Raman-active vibrational resonances $\omega_1 - \omega_2$.

The output 66 is collimated by a lens 68 and passed through an aperture 70 to reduce any undesired fluorescence which may have occured in the sample. The output 66 contains, in addition to the anti-Stokes frequencies $\omega_3$, various undesired components due to the probe pulse $\omega_1$ and the continuum pulse $\omega_{WL}$. In order to enhance the detection of the anti-Stokes frequencies, these undesired components should be removed. In the apparatus 10 of the present Invention, this is accomplished by means of dielectric reflecting filters 72 and 74. Filter 72 is a notch-type reflecting filter having its maximum reflection centered at 527 nm ($\omega_1$) and transmitting at shorter and longer wavelengths. Any additional notches should be located outside the frequency band of interest for the anti-Stokes frequencies $\omega_3$. A filter of this type is a standard item which may be obtained from Omega Optical Co. The filter 74 is a short-wavelength-pass-type reflecting filter which passes wavelengths shorter than about 510 nm. This filter is a standard item obtainable from Melles Griot Optical Co.

One or more mirrors, such as mirror 76, may be included along the optical path of the output 66 to bend the optical path into a convenient direction, as desired. An analysing polarizer 75 may be included in the optical path 66 for use in certain CARS measurements, such as the suppression of non-resonant background emissions, as is known in the art.

The filtered output 78 of the filter 74 is focused by means of a cylindrical lens 80 onto a grating spectrograph 82 which spatially disperses the output into a spectrum. The anti-Stokes spectrum developed within the spectrograph 82 is then detected and digitially recorded by an intensified vidicon system 84 (Princeton Applied Research OMA II ISIT vidicon) coupled to receive the output of the spectrograph 82 in a well-known manner.

Figure 2:
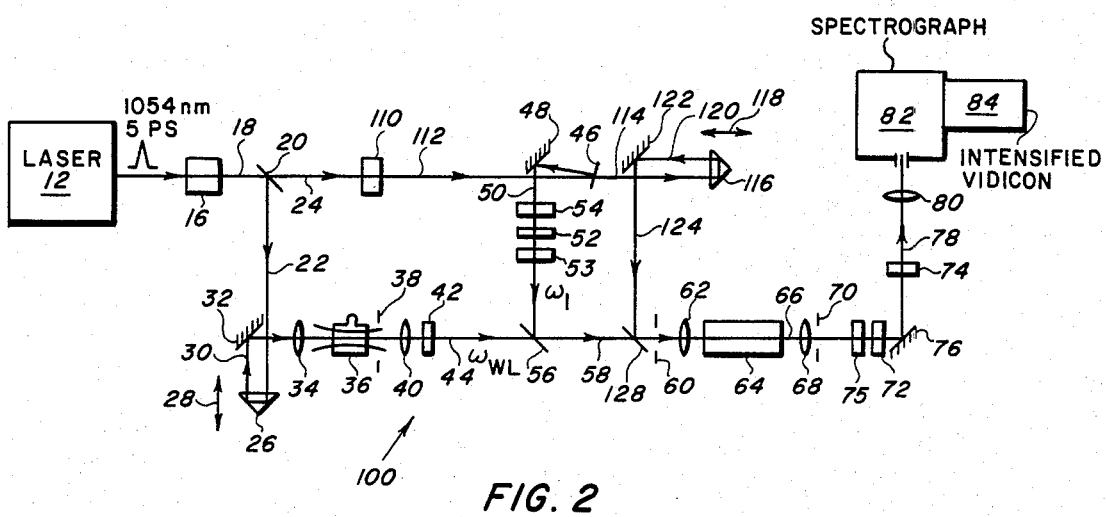
FIG. 2 schematically illustrates another preferred embodiment of the present Invention.

Certain types of spectrographic experiments such as photolysis require subjecting the sample to be analysed to an additional excitation pulse in addition to the CARS probe and continuum pulses $\omega_1$ and $\omega_{WL}$. The excitation pulse raises the sample to an excited state which is then probed by transient vibrational spectral analysis. FIG. 2 illustrates a CARS apparatus 100 according to a preferred embodiment of the present Invention wherein an ultraviolet excitation pulse is developed within the CARS apparatus 10 shown in FIG. 1.

In the CARS apparatus 100 of FIG. 2, the 527 nm pulse traveling along the optical path 24 from the spectral beam splitter 20 passes through a second-harmonic generator 110 which produces a nominal 5 picosecond output pulse 112 containing the fundamental frequency at 527 nm and the second-harmonic at 264 nm. The second-harmonic generator 110 is formed from a well known temperature-tuned 90-degree-phase-matched ammonium dihydrogen phosphate (ADP) crystal having a thickness of 5 mm.

The pulse 112 is directed onto the spectral beam splitter 46 where the 527 nm portion of the pulse is separated and directed toward the mirror 48 to ultimately form the probe pulse $\omega_1$, as described above with respect to the embodiment illustrated in FIG. 1. The 264 nm portion of the pulse 112 is separated by the beam splitter 46 to travel along an optical path 114 as the excitation pulse.

The 264 nm excitation pulse traveling along the optical path 114 is directed onto a right angle prism 116 which is mounted in a well-known manner to be movable in the directions indicated by the arrows 118. The prism 116 redirects the pulse traveling along the optical path 114 to travel along the optical path 120. Additionally, moving the prism 116 allows the length of the optical path traveled by the pulse to be adjusted thereby introducing a controllable amount of delay into the system, as will be further discussed below.

The 264 nm excitation pulse traveling along the optical path 120 is deflected by a mirror 122 to travel along an optical path 124. The optical path 124 and the optical path 58 traveled by the combined probe and continuum pulses $\omega_1$ and $\omega_{WL}$ intersect at a beam splitter 128 where the 264 nm pulse is collinearly combined with the probe and continuum pulses prior to application to the sample cell 64. The prism 116 may be moved to alter the temporal relationship between the 264 nm excitation pulse and the combined probe and continuum pulses $\omega_1$ and $\omega_{WL}$. The excitation pulse may be temporally aligned with the probe and continuum pulses or may be set to occur a given length of time prior to these pulses, as required by the experiment being performed.

The CARS apparatus 100 of FIG. 2 provides a means for generating a fourth harmonic excitation pulse within the CARS apparatus 10 shown in FIG. 1. Excitation pulses having different frequencies may be generated in a variety of manners by suitable modification of the apparatus, as should now be apparent to the skilled practitioner. Alternatively, the excitation pulse could be generated from a separate synchronously driven laser source providing a picosecond pulse temporally related to the 1054 nm output pulse 14 of the laser 12. The use of a separate laser source would allow excitation pulses to be generated at frequencies which are not harmonically or otherwise directly related to the 1054 nm fundamental pulse 14.

Figure 3:
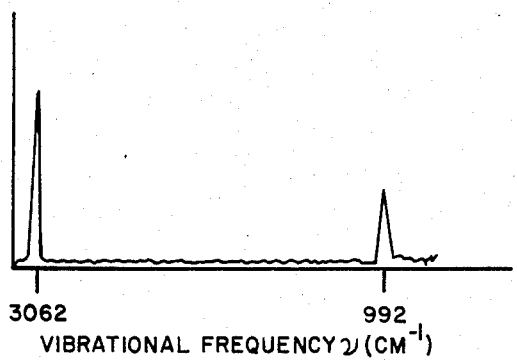
FIG. 3 illustrates a CARS spectrum of benzene obtained using the embodiment of the present Invention shown in FIG. 1.

FIG. 3 illustrates a representative CARS spectrum obtained using the CARS apparatus 10 of FIG. 1 for a sample of benzene vapor $C_6H_6$ contained within the sample cell 64 at a pressure of 60 Torr. A single 5 picosecond laser pulse was used to develope the spectrum. The prominent narrow spectral features are identified as the fully symmetric 3062 $cm^{-1}$ C—H stretch and 992 $cm^{-1}$ C—C stretch modes of ground-state benzene. The vibrational frequency range encompassed in this measurement extends well over 2000 $cm^1$.

Figure 4:
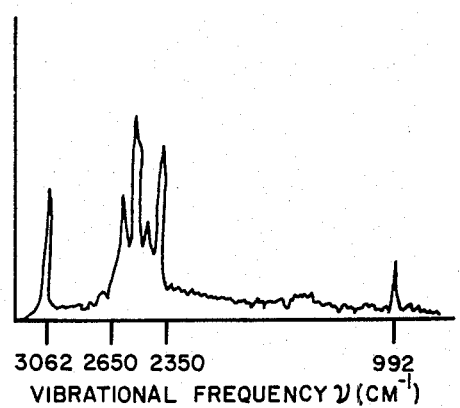
FIG. 4 illustrates a CARS spectrum of benzene obtained using the embodiment of the present Invention shown in FIG. 2.

FIG. 4 illustrates a spectrum obtained by the photolysis of benzene vapor using the CARS apparatus 100 of FIG. 2. Here the benzene sample was excited by a 264 nm excitation pulse occuring 200 picoseconds prior to the application of the probe and continuum pulses $\omega_1$ and $\omega_{WL}$. As can be observed from FIG. 2, dramatic new CARS spectral features appear in the region from 2350 to 2650 $cm^{-1}$ in addition to those spectral features shown in FIG. 1. These new spectral features are believed to arise from multiple resonant enhancements in the non-linear susceptibility of a $C_2$ product species.

Numerous modification and variations of the present Invention are possible. Other laser wavelengths may be used to drive the white-light continuum generation, as well as other pulse durations, including pulses in the sub-picosecond range, in order to obtain greater time resolution. Other appropriate probe frequencies $\omega_1$ and continuum frequencies $\omega_{WL}$ may be used, including such choices as to give resonant enhancement of sample susceptibilities. Laser-pumped dye amplifier stages may be incorporated into the apparatus of FIGS. 1 and 2 to amplify the continuum intensity in various spectral regions for improved detection of the CARS spectrum. The present Invention should not be considered to be limited to the various optical layouts shown in FIGS. 1 and 2. Any optical layout may be used which affords proper beam handling, filtering, and tuning to provide appropriate CARS pulse pairs at the sample and which enables adequate discrimination and detection of the anti-Stokes spectrum.

The present Inventor believes that the present Invention is the first application of picosecond white-light continuum pulses to CARS spectroscopy. This method enables, for the first time, an extensive broadband CARS vibrational spectrum to be obtained with a single picosecond laser pulse. Because of the extreme spectral breadth of the continuum pulse, the spectral breadth of the CARS measurement can extend over 4000 $cm^{-1}$. This method also enables picosecond time resolution between an independent excitation pulse and CARS probing pulses. Since the CARS process is emissive, signals produced by the method of the present Invention are detected against an essentially dark background, while prior art inverse Raman scattering processes require detection of an absorbed or reduced signal in the presence of a strong background.

Obviously, numerous (additional) modifications and variations of the present Invention are possible in light of the above teachings. It is therefore to be understood that within the scope of the appended claims, the Invention may be practiced otherwise than as specifically described herein.

What is claimed as new and desired to be secured by Letters Patent of the United States is:

1. A coherent anti-Stokes Raman spectroscopy (CARS) method for producing a picosecond broadband CARS vibrational spectrum of a sample comprising the steps of:

generating a probe pulse of coherent monochromatic radiation having a frequency $\omega_1$, said probe pulse having a duration on the order of picoseconds;

generating a continuum pulse of broadband radiation, said continuum pulse having a range of frequencies $\omega_{WL}$ and a duration on the order of picoseconds, said range of frequencies $\omega_{WL}$ of said continuum pulse being related to said frequency $\omega_1$ of said probe pulse such that the difference $\omega_1 - \omega_{WL}$ corresponds to a range of Raman active vibrational resonances in said sample;

spatially and temporally combining said probe pulse and said continuum pulse;

directing said combined probe pulse and continuum pulse into said sample to excite the Raman active vibrational resonances in said sample; and detecting a beam of radiation emitted by said sample, said beam of radiation including an anti-Stokes spectrum of energy characteristic of said sample.

2. The method recited in claim 1, wherein the said step of generating said continuum pulse comprises the steps of:

providing a fundamental pulse of coherent monochromatic radiation having a fundamental frequency $\omega$, said pulse having a duration on the order of picoseconds;

focusing said fundamental pulse into a liquid cell containing a continuum generating medium, said continuum generating medium producing an output pulse of broadband radiation having a range of frequencies $\omega_{WL}$ and a duration on the order of picoseconds; and filtering said output pulse to remove remanants of said fundamental pulse at said frequency $\omega$ to produce said continuum pulse.

3. The method recited in claim 2, wherein said step of focusing said pulse into said liquid cell further comprises the step of:

focusing said pulse into said liquid cell containing $D_2O$ liquid acting as said continuum generating medium.

4. The method recited in claim 2, wherein said step of focusing said pulse into said liquid cell further comprises the step of:

focusing said pulse into said liquid cell containing a 50 percent mixture of $D_3PO_4$ in $D_2O$ liquid acting as said continuum generating medium.

5. The method recited in claim 1, wherein said step of generating said continuum pulse comprises the steps of:

providing a first pulse of coherent monochromatic radiation having a frequency of $\frac{1}{2}\omega$, said first pulse having a duration on the order of picoseconds;

passing said first pulse through a first second-harmonic generator to form a second pulse, said second pulse containing a first component at a frequency $\frac{1}{2}\omega$ and a second component at a frequency $\omega$;

spatially dividing said first and second components of said second pulse into a first component pulse at said frequency $\frac{1}{2}\omega$ and a second component pulse at said frequency $\omega$;

delaying said first component pulse by a first variable amount of time relative to said second component pulse; and generating said continuum pulse from said delayed first component pulse.

6. The method recited in claim 5, wherein said step of generating said continuum pulse further comprises the steps of:

focusing said delayed first component pulse into a liquid cell containing a continuum generating medium, said continuum generating medium producing an output pulse of broadband radiation having a range of frequencies $\omega_{WL}$ and a duration in the order of picoseconds; and filtering said output pulse to remove remanants of said delayed first component pulse at said frequency $\frac{1}{2}\omega$ to produce said continuum pulse.

7. The method recited in claim 6, wherein said step of focusing said delayed first component pulse into said liquid cell further comprises the step of:

focusing said delayed first component pulse into said liquid cell containing $D_2O$ liquid acting as said continuum generating medium.

8. The method recited in claim 6, wherein said step of focusing said delayed first component pulse into said liquid cell further comprises the step of:

focusing said delayed first component pulse into said liquid cell containing a 50 percent mixture of $D_3PO_4$ in $D_2O$ liquid acting as said continuum generating medium.

9. The method recited in claim 5, wherein said step of spatially and temporally combining said probe and continuum pulses further comprises the step of:

adjusting said first variable amount of time to temporally align said continuum pulse with said probe pulse.

10. The method recited in claim 5, wherein said step of generating said probe pulse comprises the step of:

providing said first pulse of radiation such that said frequency $\frac{1}{2}\omega$ equals a frequency $\frac{1}{2}\omega_1$, said second component pulse forming said probe pulse.

11. The method recited in claim 5, wherein said step of generating said probe pulse comprises the step of:

passing said second component pulse through a frequency shifter to convert said second component pulse at said frequency $\omega$ to said probe pulse at said frequency $\omega_1$.

12. The method recited in claim 5 which further comprises the steps of:

passing said second component pulse through a second second-harmonic generator to form a third pulse, said third pulse containing a third component pulse at a frequency $2\omega$ and a fourth component at said frequency $\omega$;

spatially dividing said third and fourth components of said third pulse into a third component pulse at said frequency $2\omega$ and a fourth component pulse at said frequency $\omega$;

delaying said third component pulse by a second variable amount of time relative to said fourth component pulse;

spatially combining said delayed third component pulse with said combined probe and continuum pulses:

directing said combined delayed third component pulse and said probe and continuum pulses into said sample, said delayed third component pulse acting as an excitation pulse to raise said sample to an excited state.

13. The method as recited in claim 12, wherein said step of generating said probe pulse comprises the step of:

providing said first pulse of radiation such that said frequency $\frac{1}{2}\omega$ equals a frequency $\frac{1}{2}\omega_1$, said fourth component pulse forming said probe pulse.

14. The method recited in claim 12, wherein said step of generating said probe pulse comprises the step of:
passing said fourth component pulse through a frequency shifter to convert said fourth component pulse at said frequency $\omega$ to said probe pulse at said frequency $\omega_1$.

15. The method recited in claim 1, wherein said step of detecting said beam of radiation emitted by said sample comprises the steps of:
filtering said beam of radiation to remove remanants of said probe and continuum pulses;
focusing said filtered beam into a spectrograph to develope said anti-Stokes spectrum; and
detecting said anti-Stokes spectrum.

16. A coherent anti-Stokes Raman spectroscopy (CARS) apparatus for producing a picosecond broadband CARS vibrational spectrum of a sample comprising:
means for generating a probe pulse of coherent monochromatic radiation having a frequency $\omega_1$, said probe pulse having a duration on the order of picoseconds;
means for generating a continuum pulse of broadband radiation having a range of frequencies $\omega_{WL}$ and a duration in the order of picoseconds, said range of frequencies $\omega_{WL}$ of said continuum pulse being related to said frequency $\omega_1$ of said probe pulse such that the difference $\omega_1 - \omega_{WL}$ corresponds to a range of Raman active vibrational resonances in said sample;
means coupled to receive said probe pulse and said continuum pulse for spatially and temporally combining said pulses;
means coupled to receive said combined probe and continuum pulses for directing said combined pulses into said sample to excite the vibrational resonances in said sample; and
means coupled to receive a beam of radiation emitted by said sample in response to said excitation by said combined pulses for detecting an anti-Stokes spectrum of energy characteristic of said sample contained in said beam.

17. The apparatus as recited in claim 16, wherein said means for generating said probe pulse comprises:
first second-harmonic generator means coupled to receive a first pulse at a frequency $\frac{1}{2}\omega_1$ for producing a second pulse including components at said frequency $\frac{1}{2}\omega_1$ and at said frequency $\omega_1$, said first and second pulses having durations on the order of picoseconds; and
means coupled to receive said second pulse for spatially dividing said second pulse into a first component pulse at said frequency $\frac{1}{2}\omega_1$ and a second component pulse at said frequency $\omega_1$, said second component pulse forming said probe pulse.

18. The apparatus as recited in claim 16, wherein said means for generating said probe pulse comprises:
first second-harmonic generator means coupled to receive a first pulse at a frequency $\frac{1}{2}\omega$ for producing a second pulse including components at said frequency $\frac{1}{2}\omega$ and at a frequency $\omega$, said first and second pulses having durations on the order of picoseconds;
means coupled to receive said second pulse for spatially dividing said second pulse into a first component pulse at said frequency $\frac{1}{2}\omega$ and a second component pulse at said frequency $\omega$; and
frequency shift means coupled to receive said second component pulse for shifting the frequency of said second component pulse to said frequency $\omega_1$ and for forming said probe pulse.

19. The apparatus as recited in claim 17, wherein said means for generating said continuum pulse comprises:
a liquid cell containing a continuum generating medium, said first component pulse being focused into said cell, said cell producing said continuum pulse.

20. The apparatus as recited in claim 19, wherein said continuum generating medium comprises $D_2O$ liquid.

21. The apparatus as recited in claim 19, wherein said continuum generating medium comprises a 50 percent mixture of $D_3PO_4$ in $D_2O$ liquid.

22. The apparatus as recited in claim 16, wherein said means for spatially and temporally combining said probe and continuum pulses comprises:
delay means for delaying the generation of said continuum pulse relative to said probe pulse for temporally aligning said continuum pulse with said probe pulse.

23. The apparatus as recited in claim 19, wherein said means for spatially and temporally combining said probe and continuum pulses comprises:
delay means coupled between said means for spatially dividing said second pulse and said liquid cell for delaying said first component pulse relative to said probe pulse.

24. The apparatus as recited in claim 16, which further comprises:
means for generating an excitation pulse of coherent monochromatic radiation, said excitation pulse having a duration on the order of picoseconds; and
means coupled between said means for combining said probe and continuum pulses and said means for directing said combined probe and continuum pulses for receiving said excitation pulse and said combined probe and continuum pulses and for combining said excitation pulse with said combined probe and continuum pulses, said excitation pulse being directed into said sample along with said combined probe and continuum pulses to raise said sample to an excited state.

25. The apparatus as recited in claim 24, wherein said means for generating said probe pulse comprises:
first second-harmonic generator means coupled to receive a first pulse at a frequency $\frac{1}{2}\omega$ for producing a second pulse including components at said frequency $\frac{1}{2}\omega$ and at a frequency $\omega$, said first and second pulses having durations on the order of picoseconds;
means coupled to receive said second pulse for spatially dividing said second pulse into a first component pulse at said frequency $\frac{1}{2}\omega$ and a second component pulse at said frequency $\omega$;
second second-harmonic generator means coupled to receive said second component pulse at said said frequency $\omega$ for producing a third pulse including components at said frequency $\omega$ and at a frequency $2\omega$; and
means coupled to receive said third pulse for spatially dividing said third pulse into a third component pulse at said frequency $\omega$ and a fourth component pulse at said frequency $2\omega$, said third component pulse forming said probe pulse.

26. The apparatus as recited in claim 24, wherein said means for generating said probe pulse comprises:
- first second-harmonic generator means coupled to receive a first pulse at a frequency $\frac{1}{2}\omega$ for producing a second pulse including components at said frequency $\frac{1}{2}\omega$ and at a frequency $\omega$, said first and second pulses having durations on the order of picoseconds;
- means coupled to receive said second pulse for spatially dividing said second pulse into a first component pulse at said frequency $\frac{1}{2}\omega$ and a second component pulse at said frequency $\omega$;
- second second-harmonic generator means coupled to receive said second component pulse at said said frequency $\omega$ for producing a third pulse including components at said frequency $\omega$ and at a frequency $2\omega$;
- means coupled to receive said third pulse for spatially dividing said third pulse into a third component pulse at said frequency $\omega$ and a fourth component pulse at said frequency $2\omega$; and
- frequency shift means coupled to receive said third component pulse for shifting the frequency of said third component pulse to said frequency $\omega_1$ and for forming said probe pulse.

27. The apparatus as recited in claim 25, wherein said means for generating said excitation pulse comprises:
- means coupled to receive said fourth component pulse for delaying said fourth component pulse by a variable amount of time relative to said probe pulse and for producing said excitation pulse.

28. The apparatus as recited in claim 16, wherein said means for detecting said anti-Stokes spectrum comprises:
- means coupled to receive said beam of radiation from said sample for filtering said beam to remove remanants of said probe and continuum pulses to produce a filtered beam; and
- spectrograph means coupled to receive said filtered beam for developing said anti-Stokes spectrum from said beam.

* * * * *